United States Patent [19]

Dutcher et al.

[11] 4,140,131
[45] Feb. 20, 1979

[54] BODY TISSUE STIMULATION APPARATUS WITH WARNING DEVICE

[75] Inventors: Robert G. Dutcher, Columbia Heights; Paul Citron, New Brighton; Thomas L. Jirak, Plymouth, all of Minn.

[73] Assignee: Medtronic, Inc., Minneapolis, Minn.

[21] Appl. No.: 738,298

[22] Filed: Nov. 3, 1976

[51] Int. Cl.² ............................................. A61N 1/36
[52] U.S. Cl. ............................................ 128/419 PT
[58] Field of Search ....... 128/419 P, 419 PG, 419 PS, 128/419 R, 421, 422, 423

[56] References Cited

U.S. PATENT DOCUMENTS

| | | | |
|---|---|---|---|
| 3,253,595 | 9/1966 | Murphy, Jr. et al. | 128/419 P X |
| 3,474,353 | 10/1969 | Keller, Jr. | 128/419 PT |
| 3,523,539 | 8/1970 | Lavezzo et al. | 128/419 PG |
| 3,726,285 | 4/1973 | Bowers et al. | 128/419 PG X |
| 3,774,619 | 11/1973 | Goldberg | 128/419 PG |
| 3,783,877 | 1/1974 | Bowers | 128/419 PS |
| 3,920,024 | 11/1975 | Bowers | 128/419 PG |

FOREIGN PATENT DOCUMENTS 1082752  9/1967  United Kingdom ................. 128/419 P

*Primary Examiner*—William E. Kamm
*Attorney, Agent, or Firm*—R. Lewis Gable; Joseph F. Breimayer

[57] ABSTRACT

Apparatus for stimulating body tissue and in particular the heart, is disclosed as including a device or circuit responsive to the initiation of stimulation and/or to the failure or pending failure of a component of the stimulating apparatus to provide the patient with a perceivable stimulation to a second, different portion of body tissue. There is disclosed an impedance level detector for sensing the impedance presented between the outputs of the stimulation apparatus to provide a warning signal indicating that the output impedance falls outside a predetermined range. In particular, the impedance level detector output is sensed by a stimulation control logic to apply a first train of pulses at a first rate to an auxiliary electrode for stimulating the second portion of tissue. Further, there is included a voltage level detector for sensing when the power source voltage depletes below a predetermined level, to actuate the stimulation control logic to provide a second train of warning pulses to the auxiliary electrode, at a second, different rate than that of the first train. In this fashion, the patient not only is warned as to the pending failure or failure of a component of his pacemaker, but also is able to identify the failing component.

25 Claims, 5 Drawing Figures

FIG. IA.
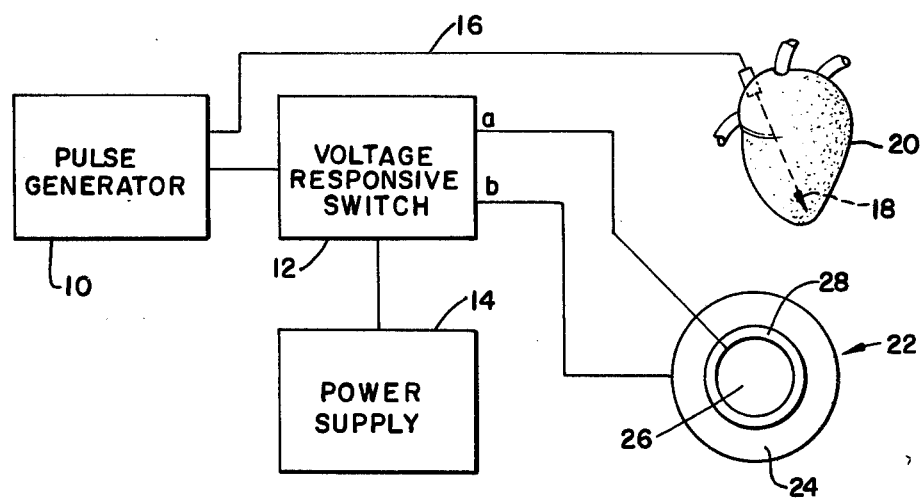
FIG. IB.
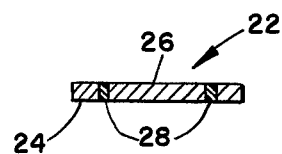

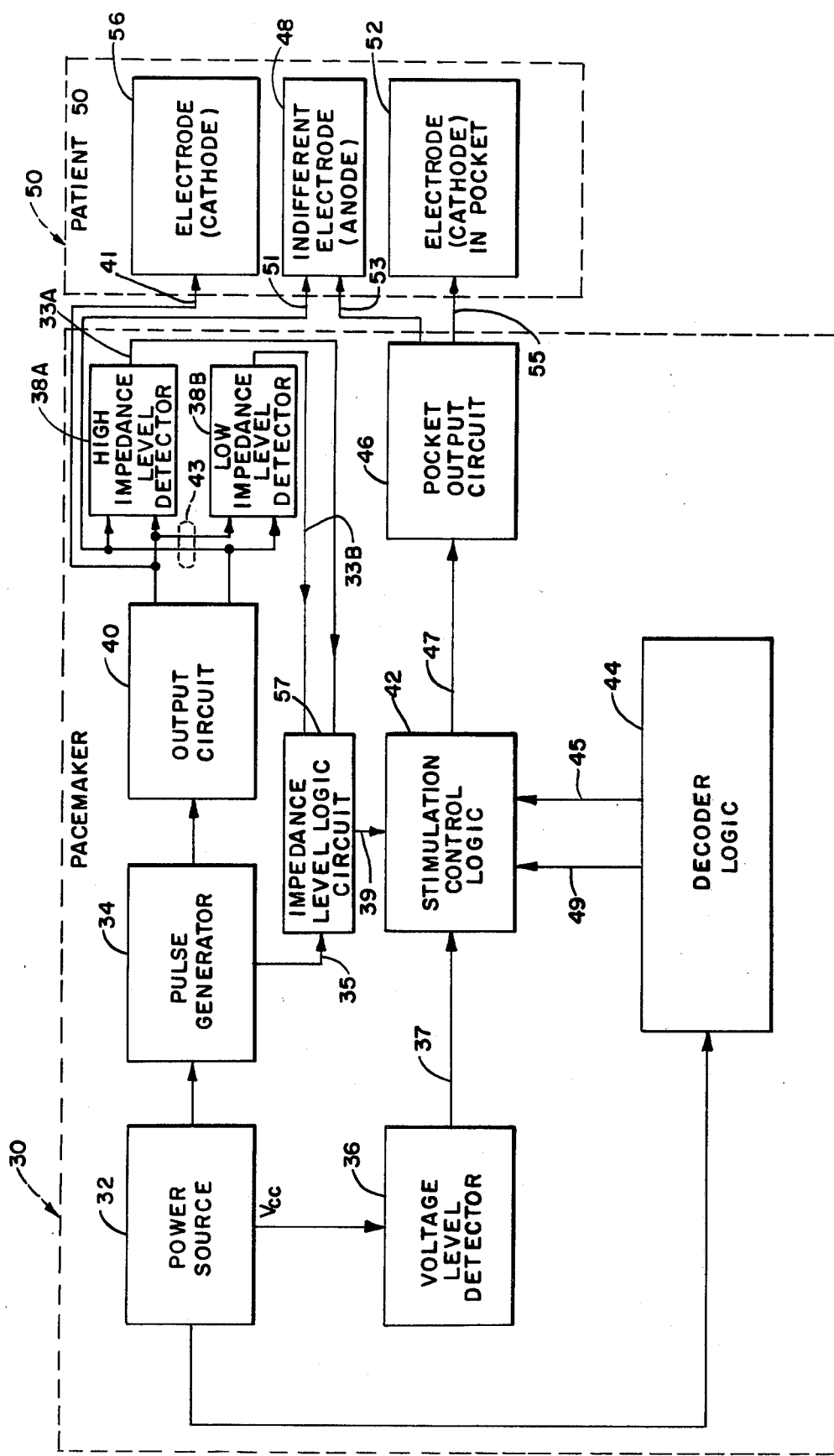

BODY TISSUE STIMULATION APPARATUS WITH WARNING DEVICE

BACKGROUND OF THE INVENTION

1. Field of the Invention

This invention relates to apparatus for monitoring and detecting a pending failure, operation of and/or inoperability of a heart pacemaker, and in particular, to apparatus for monitoring the voltage level of the pacemaker power supply, initiation of heart stimulation and/or the impedance presented to the output of the pacemaker.

2. Description of the Prior Art

Heart pacemakers such as that described in U.S. Pat. No. 3,057,356, issued in the name of Wilson Greatbatch and assigned to the assignee of this invention, are known for providing electrical stimulus to the heart whereby it is contracted at a desired rate in the order of 72 beats per minute. A heart pacemaker is capable of being implanted in the human body and operative in such an environment for relatively long periods of time, to provide cardiac stimulation at relatively low power levels by utilizing a small, completely implanted, transistorized, battery-operated pacemaker connected via flexible electrode wires directly to the myocardium or heart muscle. The electrical stimulation by this pacemaker is provided at a relatively fixed rate.

Such cardiac pacemakers of the implantable variety have found wide acceptance for heart patients suffering from complete heart block and other defects of normal conduction. As a result, the use of these pacemakers has increased the life expectancy of those patients with implants, from a 50% probability of 1 year to nearly the life expectancy of physically-comparable humans not suffering from the same heart disorder.

Typically, such cardiac pacemakers are encapsulated in a substance substantially inert to body fluids, and are implanted within the patient's body by a surgical procedure wherein an incision is made in the chest beneath the patient's skin and above the pectoral muscles or in the abdominal region, and the pacemaker is implanted therein. Due to the inconvenience, expense and relative risk to the patient's health, it is highly desired to extend the life of the power source or battery, whereby the number of such surgical procedures is limited. The resultant problem for the attendant doctor is to determine when the batteries should be replaced, keeping in mind the relative risk or probability of premature pacemaker failure due to battery depletion.

A number of solutions to this problem have been proposed, one being replacement at predetermined intervals, thus accepting an empirically determined risk or failure of the pacemaker batteries. Another proposed solution is to establish pacemaker "clinics" where photographic analysis techniques are used to detect imminent failure. These solutions are not entirely satisfactory for detecting, simply and positively, a degradation of pacemaker system performance. The risk of undetected premature failure associated with periodic replacement at predetermined intervals is obviously undesirable. Photoanalysis techniques are complicated, not positive in detection and require that the patient be physically present in the physician's office. Further, such techniques are not readily available to physician and patient on short notice, but rather, as mentioned previously, would be available only at special clinics, and, furthermore, are scheduled at relatively infrequent intervals.

In U.S. Pat. No. 3,618,615, assigned to the assignee of this invention, there is disclosed an artificial cardiac pacemaker for generating at regular intervals a train of stimulating pulses, one of which is of significantly lower energy than the other pulses. If the heart responds to the reduced energy stimulating pulse, an adequate safety factor remains, but if the heart does not respond, e.g. no beat is detected in response to the lower energy or test pulse, marginal operation and possible imminent failure is ascertained.

Another method of ascertaining the pending failure of a pacemaker energy source is described in U.S. Pat. No. 3,713,449, assigned to the assignee of this invention, describing an artificial pacemaker including means for varying selectively the pulsewidth of its stimulating pulse. Control of the pulsewidth is made preferably by a mechanism external of the body by an attending physician. By such mechanism, the physician varies the pulsewidth of the implanted pacemaker until capture is lost. As the physician has previously measured the pulsewidth at the time of pacemaker implant, the pulsewidth at a subsequent time may be varied until capture is lost, whereby the state of the battery can be determined with respect to its replacement.

In an alternative approach to the problem of accurately determining battery depletion, there are artificial pacemakers such as described in U.S. Pat. No. 3,842,844, having a battery or cell depletion indicator that increases the pulsewidth of the output signal as their batteries deplete, i.e., their voltage amplitude decreases. Further, as the power source or battery depletes, the pulse repetition rate of such artificial cardiac pacemakers also decreases. For example, at the time of implantation, an artificial cardiac pacemaker may produce stimulating pulses at 70 pulses per minute (PPM), plus or minus two beats, with a pulsewidth in the order of 0.5 msec. After a period of service illustratively in the order of 2-4 years, the PPM changes in the order of 5%-10%, i.e., a decrease of 5-7 beats from the original PPM, and the pulsewidth may increase to a value in the order of 1 msec. Dependent upon the known histories of such batteries, such a change in the pulse rate as well as a change in pulsewidth indicates that one of a plurality of (e.g. 4 or 5) cells has failed, and that it is time to replace the batteries within the implanted pacemaker to assure continued heart stimulation of a sufficient level.

Further, in the prior art, there is known a still further method for detecting and providing a manifestation indicative of the dissipation or pending failure of a heart pacemaker power supply. A primary and an auxiliary power source are used in conjunction with a diode switching circuit, which responds when the voltage level of the primary source becomes less than that of the secondary source, to apply the secondary source to a timing pulse generator. Due to the voltage characteristics of the diodes incorporated within the switching circuit, a slightly reduced voltage is applied by the secondary source to the generator, whereby the generator changes slightly its stimulus pulse rate. It appears that the slight change in pulse rate would not normally be sensed by the patient within whom such a heart pacemaker is implanted, but would require a physician to measure the pulse rate to detect a pending depletion or failure of the heart pacemaker power supply. In a further disclosed embodiment, a second set of electrodes including an indifferent electrode plate and a second electrode are disposed in body tissue remote from the heart, whereby when the voltage level of the primary power source falls below that of the auxiliary power source, the auxiliary power source is applied to the second set of electrodes whereby the body tissue between the second set of electrodes is stimulated so that the patient is made directly aware of the possibility of the failure of the heart pacemaker power source. In such an arrangement, there is required a redundant power source and there are no convenient means for de-energizing the second set of electrodes, whereby the auxiliary power source is required to energize not only the pulse generator, but also the second set of electrodes. As a result of this double load, the auxiliary power is drained fairly rapidly. Further, the disclosed excitation of the second set of electrodes would be by a DC-type battery source, providing a steady level of stimulation to the patient. In some instances, it is contemplated that the patient would be more sensitive or responsive to a modulated stimulation than that provided by this pacemaker.

Further, it is desirable to provide a warning that the pacemaker leads have failed or are about to fail. As discussed above, a pacemaker is implanted within the human body by a surgical procedure, with at least one of its leads interconnected between the pacemaker and the patient's heart. As the patient moves in terms of bending over or stretching with the pacemaker implanted within his body, the pacemaker lead will be bent continuously to the point where the conductors thereof break or split or the insulating material of the pacemaker leads deteriorates. Further, it is contemplated that during the implantation of the pacemaker, the insulating material of one of the leads may be cut, thus exposing a portion of the electrical conductor. If the pacemaker leads have failed or are about to fail, the level of stimulation to the patient's heart is reduced significantly, if not blocked altogether. Therefore, it is desirable to provide a detector or monitor circuit for detecting the impedance and to provide the patient with an indication thereof.

Further, in those patients who receive a permanently-implanted pacemaker of the "demand" type in anticipation of imminent sudden disruption of the normal conduction sequence of the heart, it is desirable to provide a warning that the pacemaker has begun to operate and is stimulating the heart. Such a warning is of particular importance for patients who have received a pacemaker prophylactically, the pacemaker being in a dormant state at the time of implantation and in the immediate period following implantation, and due to a potentially life-threatening change in the condition of the heart's conduction system, the pacemaker has begun to stimulate the heart. Such patients, upon receiving the warning, would be encouraged to seek professional (i.e., medical) assistance to assess their immediate condition.

SUMMARY OF THE INVENTION

It is therefore an object of this invention to stimulate the patient into which a heart pacemaker has been implanted, in a more efficient or noticeable manner to provide the patient with a manifestation that the heart pacemaker power source and/or some aspect of pacemaker operation is about to fail or has failed, or that the pacemaker has begun to function.

It is a further object of this invention to enable the patient or his physician to terminate the warning manifestation as provided by the heart pacemaker monitoring device so as to conserve the energy of its power source.

It is a still further object of this invention to provide a heart pacemaker incorporating a monitor to detect the failure or pending failure of its output leads.

It is still another object of this invention to provide a heart pacemaker and a power source monitoring device that does not require the addition of an auxiliary power source.

It is another object of this invention to provide a heart pacemaker with detector devices or circuits therein for detecting different conditions of pacemaker operation, and for providing distinct warning stimulation to the body tissue of the patient, whereby the patient may readily perceive the warning and the element of the pacemaker that is failing or has failed, or that the pacemaker has begun to operate.

In accordance with these and other objects, the invention comprises a heart pacemaker, with at least one monitoring or detector circuit for detecting an abnormal condition of heart pacemaker operation, to apply a warning stimulation via an auxiliary electrode to the patient's body tissue, whereby the patient may readily perceive that a component of his pacemaker has failed or is about to fail, or that the pacemaker has begun to operate. In a first aspect of the invention, there is provided a detector circuit for sensing the impedance presented between the outputs of the pacemaker, to provide a first type of warning stimulation if the load impedance, in particular the impedance of the pacemaker leads, exceeds or falls below a predetermined level. In a further aspect of this invention, there is additionally provided a voltage level detector for monitoring the voltage of the pacemaker power supply source, to provide a second type of warning stimulation to a patient to indicate a low power supply voltage. In one particular example of this invention, the rate of the warning stimulating pulses generated in response to a pending or actual failure of the pacemaker leads, is made different from that of the warning stimulation provided in response to the detection of a pending or actual failure of the power source.

In a further aspect of this invention, the warning means can be used in "demand" type pacemakers to herald the initiation of stimulation from a previous dormant state.

In a still further aspect of this invention, the heart pacemaker circuitry includes logic circuitry or means responsive to an external manipulation such as that of a magnet, which is disposed and withdrawn from the pacemaker, whereby the warning stimulation may be turned off, thus conserving the energy otherwise depleted from the power source of the pacemaker. Further, the logic means also may be responsive to a different manipulation of the magnet, such as disposing and withdrawing the magnet twice within a preselected period, to reset or reinitialize the logic means or circuitry.

BRIEF DESCRIPTION OF THE DRAWINGS

These and other objects and advantages of the present invention will become more apparent by referring to the following detailed description and accompanying drawings, in which:

FIGS. 1A and 1B are, respectively, a functional block diagram of a heart monitoring circuit or switch responsive to the voltage level of the power supply for supplying the pulsed output to either of a first or a second indifferent (or auxiliary) electrode of different size, dependent upon the voltage level of the power supply, and a side view of the second, indifferent electrode;

FIG. 2 is a block diagram of another embodiment of this invention wherein a heart pacemaker includes a first voltage level detector for sensing the voltage level of the power source and an impedance level detector for measuring the impedance presented to it by the pacemaker electrodes, both responsive to apply the pacemaker output to the second auxiliary electrode, whereby the patient is given a noticeable stimulation different from that applied to his heart;

DETAILED DESCRIPTION OF THE PREFERRED EMBODIMENTS

Figure 3:
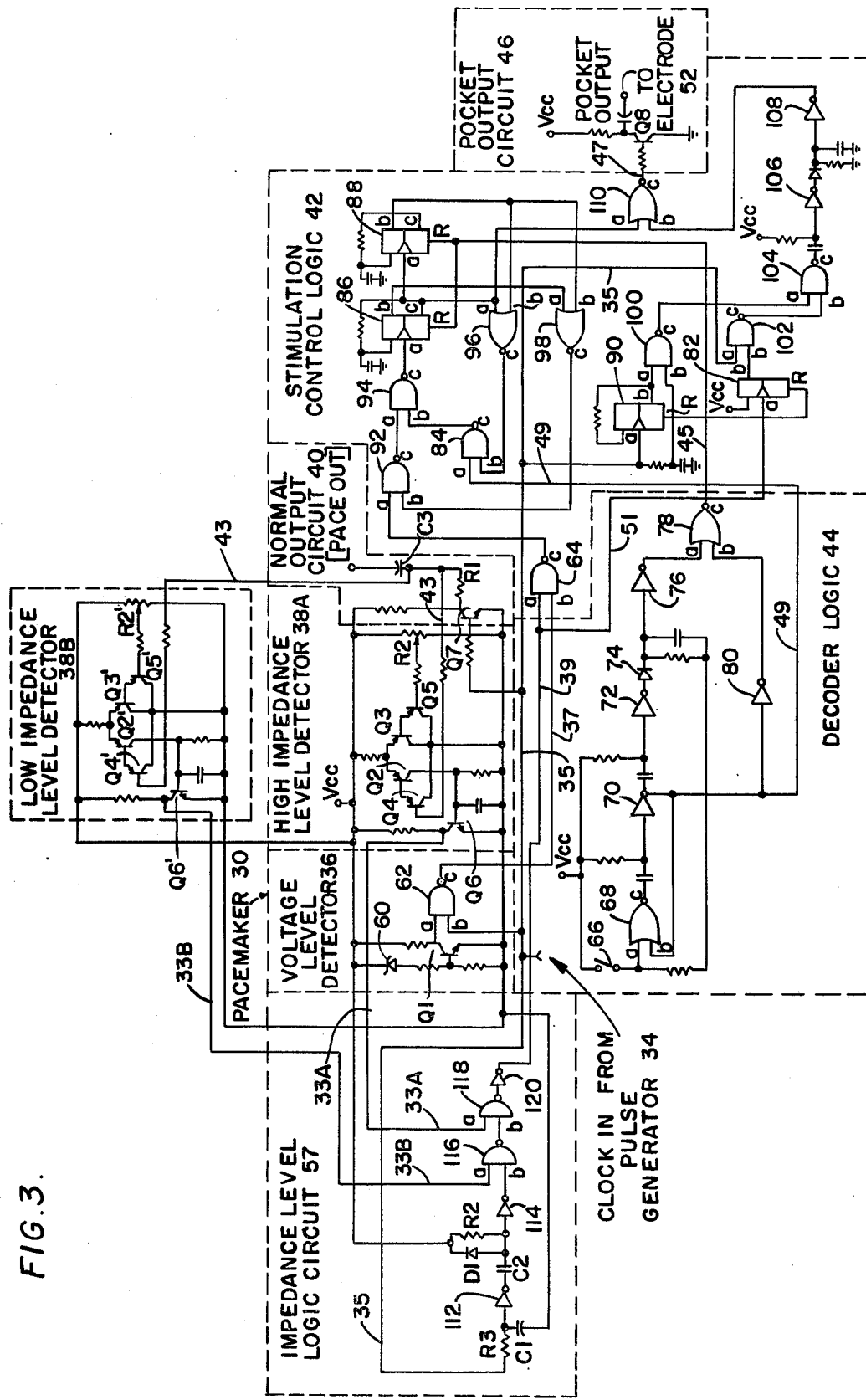
FIG. 3 is a detailed circuit diagram showing the elements and circuit arrangement of an illustrative embodiment of that circuit generally shown in FIG. 2.

Referring now to the drawings and in particular to FIG. 1A, there is shown in general block diagram form, a pacemaker circuit, such as a pacemaker Model No. 5950 or 5951 as manufactured by the assignee of this invention, modified to the extent that a voltage responsive switch 12 is incorporated therein for sensing a depletion or reduction of the voltage level of a power supply source 14 coupled thereto. Further, there is included a pulse generator 10 for generating a train of pulses at the desired stimulating rate to be applied via conductor 16 to an electrode tip 18 disposed within the patient's heart 20. The other output of the pulse generator 10 is applied by the voltage responsive switch 12, which in a normal operation applies the pulses via its output "b" to the relatively large indifferent electrode 24 of the electrode assembly 22. This illustrative embodiment of the pacemaker is of the unipolar type and its output is applied to the indifferent electrode 24, which illustratively takes the form of a circular, relatively thin conductive plate.

In operation, when the power supply 14 depletes, such as when one of its plurality of cells fails, the voltage responsive switch 12 reapplies the output of the pulse generator 10 via its output "a" to a second, smaller electrode 26 of the electrode assembly 22, whereby a more intense stimulating field is established in the vicinity of electrode 26. In particular, the current density in the vicinity of electrode 26 is increased, whereby the electric field in the vicinity of electrode 26 likewise is increased to cause surrounding tissue stimulation which can be sensed perceptibly by the patient.

As shown in both FIGS. 1A and 1B, the electrode assembly 22 includes both of the concentrically-disposed electrodes 24 and 26, which are made of an electrically-conductive material capable of being disposed within the human body, such as an alloy of platinum and iridium. In one illustrative embodiment of this invention, the areas of the circular electrodes 24 and 26 were chosen to be 10 cm$^2$ and 10 mm$^2$, respectively, and are separated, as shown in FIG. 1B, by a concentric insulating spacer 28 made of a suitable insulating material capable of being disposed within the human body, such as silicone rubber.

Referring now to FIG. 2, there is shown in block diagram form a further embodiment of this invention in the form of a pacemaker 30 comprising a power source 32 for energizing the various circuit elements of the pacemaker 30, and a pulse generator 34 of conventional design and powered by the power source 32, for generating a train of pulses at the desired rate in the order of 72 PPM. The output of the pulse generator 34 is applied through an output circuit 40 of conventional design and a conductor 43 to high and low impedance level detectors 38A and 38B, and by leads 41 and 51, respectively, to a cathode-type electrode 56, typically disposed within the heart of the patient, indicated generally by the numeral 50, and to an indifferent electrode or anode 48 placed illustratively on that first side of the pacemaker, disposed away from the patient's heart.

In accordance with one aspect of this invention, the impedance level detectors 38A and 39B are responsive to a failure of the lead 41 or 51, as by detecting the impedance presented between the outputs of the pacemaker 30 and in particular the impedance of the leads 41 and 51. The high impedance level detector 38A provides means for detecting the presence of an impedance above a first, relatively high level, indicating the breakage or rupture of the leads 41 and 51. The low impedance level detector 38B provides means for detecting the presence of an impedance and in particular the impedance presented between the leads 41 and 51, below a second, relatively low level, whereby the presence of a short between the leads 41 and 51 is detected. Thus, if an abnormally high or low impedance is detected respectively by the detectors 38A and 38B, outputs are derived thereby and applied by conductors 33A and 33B via an impedance level logic circuit 57 to a stimulation control logic circuit 42.

In a further aspect of this invention, the pacemaker 30 also includes a voltage level detector 36 for sensing the voltage level of the power source 32, whereby if the voltage level of source 32 falls below a predetermined level, an output is developed and applied by the detector 36 along a conductor 37 to the stimulation control logic 42. As will be explained in detail later, upon the occurrence of any of the aforementioned fault conditions, the stimulation control logic 42 will develop an output to be applied along conductor 47 to a pocket output circuit 46, whereby the output of the pulse generator 34 as directed along conductor 35, is modified by stimulation control logic 42 and applied by conductor 47 and pocket output circuit 46 to the indifferent electrode or anode 48 and an in-pocket, auxiliary electrode or cathode 52. The auxiliary electrode 52 may be disposed on a second side of the pacemaker 30 opposite its first side. Thus, stimulation is established between the electrodes 48 and 52 to the patient's tissue adjacent the pacemaker pocket so that he will perceive recognizably a manifestation that a failure or pending failure condition has been detected within his pacemaker 30. In normal operation, the pacemaker 30 applies its train of stimulating pulses via leads 41 and 51 to the electrodes 56 and 48 to stimulate the patient's heart to contract and expand at a corresponding rate. The patient does not normally sense this stimulation as applied to his heart, other than to notice that his heart is beating at the controlled rate. By contrast, when a failure or pending failure is detected, electrical stimulation is applied via the leads 53 and 55 to the electrodes 48 and 52 to stimulate a second or another portion of the patient's body, e.g. the tissue in terms of subcutaneous and muscle surrounding the pacemaker pocket, that is sensitive to such electrical stimulation whereby the patient perceives the warning that there is a pending failure or failure of his pacemaker. As shown in FIG. 2, there are distinct output circuits or switching means 40 and 46 for applying electrical stimulation to the electrodes 56 and 48, and 48 and 52. As a result, there is increased separation therebetween to thereby lessen the possibility of an undesired transfer of electrical stimulation between the sets of electrodes. Otherwise, there would be a possibility that the heart stimulation could be applied to the electrodes 48 and 52, whereby the patient would perceive a false warning.

In addition, decoder logic 44 is incorporated into the pacemaker 30, whereby a suitable, non-intrusive means may be used to deactuate the stimulation control logic 42, whereby the output of the pulse generator 34 no longer is applied to the electrodes 48 and 52 to provide the patient with a warning. Further, the decoder logic 44 permits the physician to reset or reinitialize the stimulation control logic 42. Prior to the pacemaker installation operation, the pacemaker 30 operating to produce output pulses without its leads inserted therein, whereby the impedance level detector 38A responds to the absence of the leads, i.e., a high impedance condition, to actuate the stimulation control logic 42 to provide warning stimulation. Thereafter, the physician inserts the leads 41 and 51 and actuates the decoder logic 44 to reset the stimulation control logic 42 to remove the warning stimulation and to begin normal operation of the pacemaker 30.

After the pacemaker 30 has been connected to its leads 41, 51, 53 and 55 and is placed into the pulse generator pocket formed within the patient's body 50, a conventional pacemaker magnet (not shown) provided with the pacemaker 30 is twice applied/removed to/from the pacemaker 30 within a specified time period (e.g., three seconds). The magnet being twice applied to the pacemaker 30 will twice close and open the magnetic reed switch 66 (see FIG. 3) incorporated within the decoder logic 44 such that two pulses are developed by the switch decoder logic 44, which in turn applies a reset pulse to the stimulation control logic 42 causing the logic 42 to assume its initial state. The implant procedure then can be completed. The pulse generator 34 will function as a conventional unit to apply electrical stimulation via normal output circuit 40, until either of the following events occurs:

(1) the voltage of the power source 32 decreases to some predetermined level, or (2) the lead impedance falls outside a predetermined range.

If the power source voltage decreases sufficiently, the voltage level detector 36 will detect this event and provide a signal via conductor 37 to the stimulation control logic 42. The control logic 42 responds to this input and provides an output signal via conductor 47 to the pocket output circuit 46 at a rate one-half that of the normal pacemaker output. As a result, output pulses will be delivered at a rate one-half that of the normal pulse generator output to the electrode system comprised of the pocket electrode 52 and the indifferent electrode 48. The output stimulus level will be sufficiently large to cause the patient perceivable tissue stimulation in the vicinity of the pocket electrode 52. This tissue stimulation will continue to provide notification to the patient of an impending power source failure (even if the voltage level should return to a value above the predetermined level), until the physician or patient disables the output by the single application of a magnet. Before disabling the output, the patient should inform his physician about the stimulation so that he can perform or instruct the patient to perform the following:

(1) Note the rate of stimulation and thereby determine the failure mode.

(2) Disable the stimulation logic control and then cause normal heart stimulation, by applying a magnet one time to the pulse generator site, thus placing a smaller load on and extending the life of the power source 32.

A single application of a magnet causes the magnetic reed switch within decoder logic 44 to close/open once such that a single signal pulse is applied by the switch decoder logic 44 to the pocket stimulation control logic 42, causing the control logic 42 to latch in one state preventing further stimulating signals from being provided to the pocket output circuit 46 and preventing further processing of signals originating from either the voltage level detector 36 or the impedance level detectors 38A and 38B. In other words, once pocket stimulation has been initiated and then turned off by a single application of the magnet, there will be no further warning stimulation applied to the pocket electrode 52 (even if the voltage level detector 36 or the impedance level detectors 38A and 38B indicates that it should) unless the stimulation control logic 42 has been reinitialized by applying a magnet twice.

If the lead impedance falls outside a predetermined range, the impedance level detectors 38A and 38B detect this event and apply a signal by conductor 39 to the stimulation control logic 42. The control logic 42 is responsive to this input and delivers a train of stimulating pulses along conductor 47 and the pocket output circuit 46 to the pocket electrodes 48 and 52 at a rate equal to that of the normal pacemaker output, thereby causing perceivable tissue stimulation of the pocket tissue. As with the pocket stimulation due to power source failure, it will continue to occur until the patient or physician resets the control logic 42 by applying a magnet once. After pocket stimulation has occurred due to an increase in lead impedance or a decrease in the power source voltage, the pulse generator and lead system should be checked for possible failure.

Referring now to the detailed, illustrative implementation of the circuit of the pacemaker 30 as shown in FIG. 3, the voltage level detector 36 comprises a transistor Q1 whose base is biased to a relatively constant potential by zener diode 60. The output of transistor Q1 is applied to "a" input of NAND gate 62. Further, the relatively high clock pulses as derived from the pulse generator 34 are periodically applied by conductor 35 to the "b" input of NAND gate 62. It is understood that the detailed circuitry of the pulse generator 34 may be similar to that incorporated into the MEDTRONIC ® pulse generator Model No. 5951 or 5950. In operation, input "b" of NAND gate 62 is normally "low" in the absence of a clock signal and the voltage $V_{CC}$ as derived from the power source 32 is normal or relatively high and is applied to the collector of transistor Q1, to bias it "on". A relatively low potential is thus applied to the "a" input of NAND gate 62, thereby causing its output "c" to remain relatively "high" even when a "high" clock pulse is applied to input "b". However, when the battery voltage $V_{CC}$ decreases below a predetermined level, the voltage applied to the collector of transistor Q1 turns transistor Q1 off, whereby the voltage applied to the "a" input of NAND gate 62 increases, enabling NAND gate 62 whereby the relatively high clock pulses derived from pulse generator 34 are permitted to pass therethrough, to be inverted and applied to conductor 37.

The high impedance level detector 38A, as shown in FIG. 3, comprises a differential amplifier comprised of transistors Q2, Q3, Q4 and Q5, with the base of transistor Q4 coupled to sense the voltage drop across resistor R1, which is indicative of the impedance imposed upon the heart pacemaker output of the normal output circuit 40. The output of the differential amplifier is taken from the collector of transistor Q2 and applied to the base of transistor Q6. Further, it can be seen that the clock pulses as derived from the clock pulse generator 34 are applied to turn "on" the output transistor Q7 to discharge the output capacitor C3 through the patient's heart. In operation the differential amplifier compares the voltage drop across resistor R1 during discharge of capacitor C3 with that constant reference voltage established by the voltage divider formed by resistor R2. Noting that resistor R2 is variable, it is adjusted to set a voltage corresponding to the threshold level of the undesirably high impedance. In normal operation, when the impedance placed upon the pacemaker output is normally low, in the order of 500 ohms, a relatively high potential across resistor R1 and transistor Q7 is applied to the base of transistor Q4, thereby turning transistors Q2 and Q4 off, thereby preventing transistor Q6 from being turned on; thus, transistor Q6 is disabled and "high" power supply voltage $V_{CC}$ is applied to input "a" of NAND gate 118 to block the passage of clock signals. As the output impedance increases toward a predetermined, impedance measured against resistor R2, e.g. 2,000 ohms, the voltage drop across resistor R1 decreases due to a decrease in the output current, whereby transistors Q2 and Q4 are turned on and subsequently, transistor Q6 is turned on. Thus, when the impedance as presented to the output of the pacemaker increases above the predetermined level, transistors Q2, Q4 and Q6 are turned on to provide a "low" signal to input "a" of NAND gate 118 to permit the clock signal as derived from conductor 35 to pass through the logic circuit 57.

The low impedance level detector 38B is identical in circuitry with the high impedance level detector 38A, having its corresponding elements designated by like characters with a prime (') attached thereto. Briefly, the voltage drop across the resistor R1 and transistor Q7 is applied to one input of a differential amplifier comprised of transistors Q2', Q3', Q4' and Q5' and is compared with a reference potential as set by resistor R2'. As explained above, the low impedance level detector 38B provides in conjunction with the impedance level logic circuit 57, which will be explained in detail later, an indication of when an electrical short circuit appears across the pacemaker output leads 41 and 51. In an illustrative embodiment of this invention, the resistor R2' is set to represent an impedance of about 50 ohms. If a lead impedance is high or normal, the voltage drop across resistor R1 and transistor Q7 is less than that across resistor R2', and transistors Q2', Q4' and Q6' are conductive. Therefore, the "low" emitter-collector voltage drop across conducting transistor Q7 is applied to input "a" of NAND gate 116. But if lead impedance is low, then transistors Q2', Q4' and Q6' are not conductive, and "high" voltage near $V_{CC}$ is applied to input 'a' of NAND gate 116.

As shown in FIG. 3, the impedance level logic circuit 57 provides, as will now be explained, a logic or decoding process with respect to the outputs of the high impedance level detector 38A and the low impedance level detector 38B, whereby the stimulation control logic 42 is provided with a suitable indication of whether a high or low impedance level is presented to the pacemaker output leads 41 and 51. In particular, the high clock signal as derived from the pulse generator 34, is applied via conductor 35 to a resistor R3, an inverter 112, a capacitor C2 and a second inverter 114 to the "b" input of NAND gate 116. The output of NAND gate 116 is applied to the "b" input terminal of NAND gate 118. Further, a first, delay circuit is formed by resistor R3 and capacitor C1, having values selected to provide a delay of the input clock signal in the order of 50 $\mu$sec. A second, timing circuit is formed by capacitor C2 and resistor R2, resistor R2 being connected between the point of interconnection of capacitor C2 and inverter 114 to the voltage $V_{CC}$. In its decoding operation, the NAND gates 116 and 118 and inverter 120 serve to provide outputs via the conductor 39 to the stimulation control logic 42. If a relatively high impedance condition is detected in the pacemaker output leads 41 and 51, the high impedance level detector 38A provides a clock output to the "a" terminal of NAND gate 118, and the low impedance level detector 38B provides a "low" signal to the "a" terminal of NAND gate 116. The delayed clock pulse as derived from the inverter 114 is a positive-going pulse "high" potential applied to the "b" input of NAND gate 116. The NAND gate 116 responds to the "low" and "high" input signals by representing a high potential output at terminal "b" of NAND gate 118. NAND gate 118 responds to the "low" and "high" input potentials and its output likewise will go high, to be inverted by inverter 120 to apply a low input via conductor 39 to the stimulation control logic 42.

In the stiuation where a normal impedance in the order of 500 ohms is presented to the pacemaker output leads 41 and 51, a "high" signal on conductor 33A will be derived from the high impedance level detector 38A. However, since the resistor R2' of the low impedance level detector 38B has been set to detect impedance levels above a predetermined lower level, e.g. 50 ohms, a "low" signal will appear on and conductor 33B and be applied to the "a" input of NAND gate 116. The clock signal applied to the "b" input of NAND gate 116, is also positive-going, so that a "high" output results from NAND gate 116 at the "b" input of NAND gate 118. NAND gate 118 responds to the two "high" inputs by developing a "low" output that is inverted by invertor 120 to a "high" signal applied to the stimulation control logic 42.

If a short or low impedance condition is detected by the low impedance level detector 38B, and a high signal is applied via conductor 33B to the input "a" of NAND gate 116. The occurrence of the "high" signal at input "b" thereof causes the output to go "low" providing a "low" input potential at input "b" of NAND gate 118. During normal and low impedance conditions, the input "a" of NAND gate 118 is "high", and therefore NAND gate responds by providing a "high" output signal that is inverted by 120.

Thus, only when lead impedance is normal will a "high" output signal be provided to input "a" of NAND gate 64 of the stimulation control logic 42.

The operation of the first delay circuit as comprised of resistor R3 and capacitor C1, and the second timing circuit comprised of the resistor R2 and capacitor C2, both of the impedance level logic circuit 57, now may be more readily appreciated in view of the above description of the operation of circuit 57. The aforementioned circuits assure a synchronization or timing of the measurement as performed by the impedance level detectors 38A and 38B, to correspond with the application of the stimulating pulses as derived through transistor Q7, resistor R1 of the output circuit 40, to ensure that the period of measurement coincides in time with the maximum peak current of the output stimulating pulses. Further, the second timing circuit C2 serves a somewhat similar function in that it provides a timing function with respect to the clock pulses derived from the pulse generator 34, permitting the circuit 57 to remain enabled for a period of only 100 μsec, the effective period during which the impedance level detectors 38A ad 38B are permitted to measure the current and thus the impedance as presented between the output leads 41 and 51. After the second timing period, the application of the clock pulse via conductor 35 is terminated by the second timing circuit, to ensure that erroneous readings are not taken, after the current as directed through transistor Q7 and resistor R1 and capacitor C3 would otherwise tend to be attenuated.

In FIG. 3, there is further shown the decoder logic 44 comprising a normally open reed switch 66 which may be closed, typically by the physician, by disposing in proximity thereto and withdrawing a magnetic member, whereby the reed switch 66 is closed passing a magnet over it. As will be explained in greater detail later, a single pass of the magnet (not shown) closes switch 66 and causes the pocket stimulation control logic 42 to be latched or turned off, thus disabling the application of the warning stimulation derived from the pulse generator 34 to the electrodes 48 and 52. In a second mode of operation, if the reed switch 66 is actuated twice, as by disposing and withdrawing a magnet twice within a selected period, e.g. three seconds, an output signal is derived from the decoder logic 44 to reset or reinitiate the pocket stimulation control logic 42. As seen in FIG. 3, the reed switch 66 is interconnected to pin "a" of NOR gate 68, the output of which is applied to the input of inverter 70. In turn, the output terminal of inverter 70 is applied in common to the input of inverter 72, the output of which is applied via a diode 74 to the input of inverter 76. Further, the output of inverter 70 also is applied to the input of inverter 80, whose output is applied to a second input terminal "b" of NOR gate 78, while a second input as derived from inverter 76 is applied to the first input terminal "a" of NOR gate 78.

In a first mode of operation of the decoder logic 44, the reed switch 66 is momentarily closed and opened once to apply the voltage $V_{CC}$ to the input terminal "a" of the NOR gate 68, thus initiating the one-shot formed by the NOR gate 68 and the inverter 70. As a result, a positive pulse is derived from the output of inverter 70 and is applied to the "b" input of NOR gate 68, inverters 72 and 80 the "a" input of and NAND gate 84. The output pulse applied along conductor 49 to the input terminal "a" of NAND gate 84 serves, as will be explained in detail later, to latch the pocket stimulation control logic 42 in its "off" state. The pulse applied to inverter 80 is inverted thereby and applied to the second input terminal "b" of NOR gate 78. The output derived from the output of the inverter 76 is of the preselected duration, e.g. three seconds, and its arrival at input "a" of NOR gate 78 is delayed such that it occurs only after the pulse input to input "b" of gate 78 has disappeared. Thus, if the reed switch 66 is only actuated a single time within the preselected period, the NOR gate 78 remains disabled, and no actuating output is derived from its output terminal "c" to be applied to conductor 45.

In a second mode of operation, the reed switch 66 is momentarily closed and opened twice during the selected period, whereby the sequence of events as explained above occurs during the first closing and opening. Thereafter, the second closing and opening of the reed switch 66 initiates the one-shot formed by the NOR gate 68 and the inverter 70 to provide an output pulse which is inverted by the inverter 80 and applied to the input "b" of NOR gate 78, whereby both inputs "a" and "b" of NOR gate 78 are held low, whereby its output "c" is driven high. As seen in FIG. 3, the output "c" of NOR gate 78 is connected via conductor 45 to the reset terminals R of the flip-flops 82, 90, 88 and 86 of the pocket stimulation control logic 42. When conductor 45 goes high, these flip-flops are reset, thus reinitializing the pocket stimulation control logic 42.

As shown in FIG. 3, the pocket stimulation control logic 42 receives input signals from the voltage level detector 36 via conductor 37 to the input "b" of NAND gate 64, from the impedance level detectors 38A and B via detector 57 and conductor 39 to the input terminal "a" of NAND gate 64, via conductor 51 to input "a" of flip-flop 82, and from decoder logic 44 via conductor 49 to input "a" of NAND gate 84. The inputs "a" and "b" of NAND gate 64 are normally in their "high" state; if either or both of inputs "a" or "b" of NAND gate 64 goes low, indicating an abnormal lead impedance or power source voltage its "c" output will go high. As shown in FIG. 3, the output "c" of NAND gate 64 is connected to the input "a" of NAND gate 92, the output "c" of which is in turn connected to input "a" of NAND gate 94. The output "c" of NAND gate 94 is connected to an input "a" of flip-flop 86, whose output "c" is coupled to input "a" of flip-flop 88. In turn, the output "b" of flip-flop 88 is connected to each of inputs "b" of NOR gates 96 and 98, whereas the inputs "a" thereof are connected, respectively, to terminals "c" and "b" of flip-flop 86. The outputs "c" of NOR gates 96 and 98 are connected, respectively, to input "b" of NAND gate 84 and input "b" of NAND gate 92.

The clock pulses as derived from generator 34 via conductor 35 are applied to input "a" of flip-flop 90 and to input "a" of NAND gate 102. The output "b" of flip-flop 90 is applied to input "a" of NAND gate 100, whose output "c" is applied to input "a" of NAND gate 104. The output of the impedance level logic circuit 57 is applied via conductors 39 and 51 to input "a" of flip-flop 82, whose output "b" is applied to input "b" of NAND gate 102, whose output "c" in turn is applied to input "b" of NAND gate 104. In turn, the output "c" of NAND gate 104 is coupled to the input of inverter 106, whose output likewise is coupled to the input of inverter 108. The output of the inverter 108 is applied to a second input "b" of NOR gate 110, whereas its first input "a" receives an input signal from the output "c" of flip-flop 86. The output "c" of NOR gate 110 forms the output of the pocket stimulation control logic 42 and is coupled via conductor 47 to the pocket output circuit 46, which comprises transistor Q8 and whose output is taken from the collector of transistor Q8 and applied to the pocket electrode 52.

When the input "a" of NAND gate 92 goes high, the following sequence of events will occur (assuming no instances of a magnet being applied other than during initialization):

(1) Output of NAND gate 92 goes low during the clock pulse, since input "b" of NAND gate 92 is initially "high".

(2) NAND gate 92 going low causes NAND gate 94 to go high during the clock pulse, since input "b" thereof is initially "high".

(3) NAND gate 94 applies a positive high signal to input "a" of flip-flop 86, toggling flip-flop 86 such that its output "b" switches from an initial low state to a new, "high" state until it again is toggled.

(4) Flip-flop 88 remains in its initial state with its outputs "b" low and output "c" high, since the flip-flop 88 will not respond to the negative pulse originating from output "c" of flip-flop 86.

(5) NOR gate 96 responds to the low output "c" of flip-flop 86, to switch from its low output state to its high output state and remains latched in this state until either flip-flop 86 or 88 is toggled.

(6) NAND gate 84 remains in its initial high state unless its input "a" goes high as the result of a magnet being applied and a high signal being received via conductor 49 from the decoder logic 44, as explained above.

(7) NOR gate 98 responds to the high output "b" of flip-flop 86, to switch from its high to its low state and remains latched in this state until flip-flop 86 again is toggled.

(8) NAND gate 92 responds to the low output "c" of NOR gate 98, to be latched in its high state since its input "b" will be latched low.

The remaining sequence of events occurring during the first clock pulse following an input from one of the detectors 36 and 38, depends upon which failure mode has been detected. If only a power source failure as indicated by the output of voltage level detector 36 has been detected, then the following sequence will occur:

(9) In response to a high pulse of the clock signal as applied to its input "a", flip-flop 90 is toggled and its output "b" is switched from its low to its high state or vice versa, depending upon its initial state. For the purpose of this discussion, assume that output "b" switches from a "low" to a "high" state.

(10) Flip-flop 82 remains its "low" initial state at its output "b" since no input will have been received from the impedance detector circuit 38.

(11) NAND gate 100 responds to the "high" output "b" of flip-flop 90 to switch from its high to its low state during the clock pulse.

(12) NAND gate 102 will remain latched in its high state, since the input to its terminal "b" from flip-flop 82 is latched low.

(13) NAND gate 104 changes from its "low" to its high state during the clock pulse and back to a "low" state following the pulse of the clock signal as transmitted through flip-flop 90 and NAND gate 100.

(14) When NAND gate 104 switches back to its "low" state after being in a "high" state, the one-shot formed by inverters 106 and 108 is triggered. As a result, the inverter 108 changes from its normally "high" to its "low" state for a time period established by the values of the discrete components in the one-shot circuitry.

(15) During the period that the inverter 108 is in its "low" state, NOR gate 110 switches to its "high" state, since input "a" of NAND gate 110 is latched in its low state by the "low" output "c" of flip-flop 86.

(16) During the period that NOR gate 110 is in its "high" state, transistor Q8 of pocket output circuit 46, is turned "on" and thus a pulse of energy will be discharged through the pocket electrode circuit including electrode 52.

On the other hand, if only an impedance outside the prescribed range is detected, then the following sequence of steps occurs in addition to the sequences described above:

(17) Flip-flop 82 receives an input via conductors 39 and 51 from the impedance level detector 38, to be toggled such that its output "b" switches from its "low" to its "high" state.

(18) The "high" output "b" of flip-flop 82 enables NAND gate 102, permitting NAND gate 102 to switch to its "low" state during the clock pulse.

(19) NAND gate 104 changes from its "low" to its "high" state during the clock pulse and back to its "low" state following the clock pulse derived via conductor 35.

After step 19, a sequence of steps similar to steps 14-16 will be carried out. In summary, the "high" output "c" derived from NAND gate 102 causes NAND gate 104 to switch to its "low" state, triggering the one-shot formed by inverters 106 and 108. The "low" output from the inverter 108 switches NOR gate 110 to its "high" state, i.e. the NOR gate 110 is enabled to permit the passage of the clock pulses through the pocket output circuit 46 to the electrode 52.

The steps 1-19 described above are those that occur within the circuitry of the pocket stimulation control logic 42 during the application of the first clock pulse following detection of an impending failure and circuit initialization; at this point in time, the magnet has not been applied to actuate the reed switch 66 of the decoder logic 44, other than during circuit initialization. The following steps occur during the second clock pulse as applied via conductor 35, again the second clock pulse as applied via conductor 35, again assuming that the magnet has not been disposed to actuate the reed switch 66:

(20) NAND gate 64 is switched to its "high" state during the second clock pulse, if one of the failure modes still is being detected as indicated by outputs on one of the conductors 37 or 39.

(21) The output states of gates 92, 84, 94, 98 and 96 and flip-flops 86 and 88 will be unaffected during the second pulse.

The remaining sequence of events occurring during the second pulse depends upon which failure mode has been detected. If only a power source failure has been detected, then the following sequence will occur:

(22) Flip-flop 90 will toggle in response to the second clock pulse switches from its "high" to its "low" state. This will occur provided the state switch assumed in step 9, above, does occur.

(23) NAND gate 100 remains in its "high" state, since its input "a" is latched "low".

(24) NAND gate 104 remains in its low state, in that a "low" signal from NAND gate 100 is applied to its input "a".

(25) The one-shot formed by inverters 106 and 108 is not triggered. Thus, the inverter 108 remains in its "high" state.

(26) Thus, NOR gate 110 remains in a "low" state, in that a "high" signal is applied from the inverter 108 to its input "b".

(27) As a result of NOR gate 110 being in its "low" state, transistor Q8 remains off during the second pulse. In reviewing the operation of the pocket stimulation control logic 42, it is understood that flip-flops 90 and 82 permit the passage of the clock signals therethrough to be applied via NOR gate 110 to the pocket output circuit 46, in response to the outputs of the voltage level detector 36 and the impedance level detector 38, respectively. Thus, when the detector 36 indicates a pending failure, as explained above, the flip-flop 90 responds to only every other clock pulse. As a result, the warning stimulation pulses are applied to the patient at a rate equal to one-half of that of the train of pulses applied to the patient's heart.

If only an impedance increase has been detected as by detector 38, then the following sequence will occur during the second clock pulse:

(28) Flip-flop 82, having previously been toggled by the first clock pulse, will not be toggled by the second clock pulse, and therefore its output "b" will remain in a high state. With a "high" signal applied to its input "b", NAND gate 102 is switched to its low state during the next clock pulse, and the sequence of events as explained in steps 18 and 19 and thereafter steps 14 to 16 will take place. Briefly, a low output is derived from NAND gate 102 to actuate NAND gate 104 to its "high" state and then back to its "low" state following the next clock pulse, thus triggering the one-shot formed by inverters 106 and 108, whereby a "low" input signal is applied to NOR gate 110, switching it to its "high" state, with the result that transistor Q8 is turned on to provide a pulse of energy to the pocket electrode 52.

Steps 20 and 21 will occur for each further clock pulse. The remaining sequence of events occurring depends upon the failure mode detected. If only a power source failure has been detected, then the sequence of events occurring will alternate with each clock pulse. One clock pulse will result in steps 9-16 occurring and the next clock pulse will result in steps 22-27 occurring. This process will be repeated for succeeding clock pulses. If an impedance outside the prescribed range has been detected, then steps 17-19 and 14-16 will occur for each suceeding clock pulse. Thus, if a power source failure is detected by the voltage level detector 36, a train of warning pulses will be provided at a rate one-half that of the heart stimulating pulses by the pocket stimulation control logic through the pocket output circuit 46 to the auxiliary electrode. By contrast, the pocket stimulation control logic 42 responds to the output of the impedance level detectors 38A and 38B to provide a train of warning pulses at a rate equal to that of the heart stimulating pulses. The patient is able to perceive the different rates of warning pulses and therefore is able to identify which component, i.e., either the power source or the leads, is about to fail or has failed.

The steps described above will continue for succeeding clock pulses until a magnet is applied to actuate the reed switch 66 of the decoder logic 44 to turn the stimulation off. When a magnet is applied/removed once after the pocket stimulation control logic 42 has been actuated to provide warning stimulation to electrode 52, the following sequence of steps occurs:

(29) NAND gate 84 responds to a signal derived from inverter 70 of the decoder logic 44 via conductor 49, to switch from its "high" to its "low" state and back to its high state, when the magnet is applied and withdrawn.

(30) NAND gate 94 switches from its "low" to its "high" state in response to the "c" output of NAND gate 84.

(31) Flip-flop 86 is toggled in response to the output "c" of NAND gate 94, such that its output "b" assumes a "low" state and its output "c" a "high" state.

(32) Flip-flop 88 is toggled in response to the "high" output "c" of flip-flop 86, such that its output "b" assumes a "high" state and its output "c" a "low" state.

(33) NOR gate 96 is latched in a "low" state since the "high" output "b" of flip-flop 88 is applied to its "b" input.

(34) NAND gate 84 is latched high in response to the "low" output "c" of NOR gate 96 and thus inputs to its input "a" will have no further effect.

(35) NOR gate 98 is latched "low" since the low "b" output of flip-flop 86 is applied to its "a" input.

(36) NAND gate 92 is latched "high" in response to the "low" input from NOR gate 98 and thus inputs from detector circuits and NAND gate 64 will have no further effect.

(37) NOR gate 110 is latched "low" since the "high" output "c" of flip-flop 86 is applied to its input "a". Thus, transistor Q8 is turned "off" and remains so, thereby terminating tissue stimulation.

In summary, once the magnet is applied/removed a single time, the tissue stimulation will be terminated and will not occur again (even if the detector circuits indicate that it should) until the logic has been reset by twice applying/removing a magnet within a selected period, e.g. three seconds.

Figure 4:
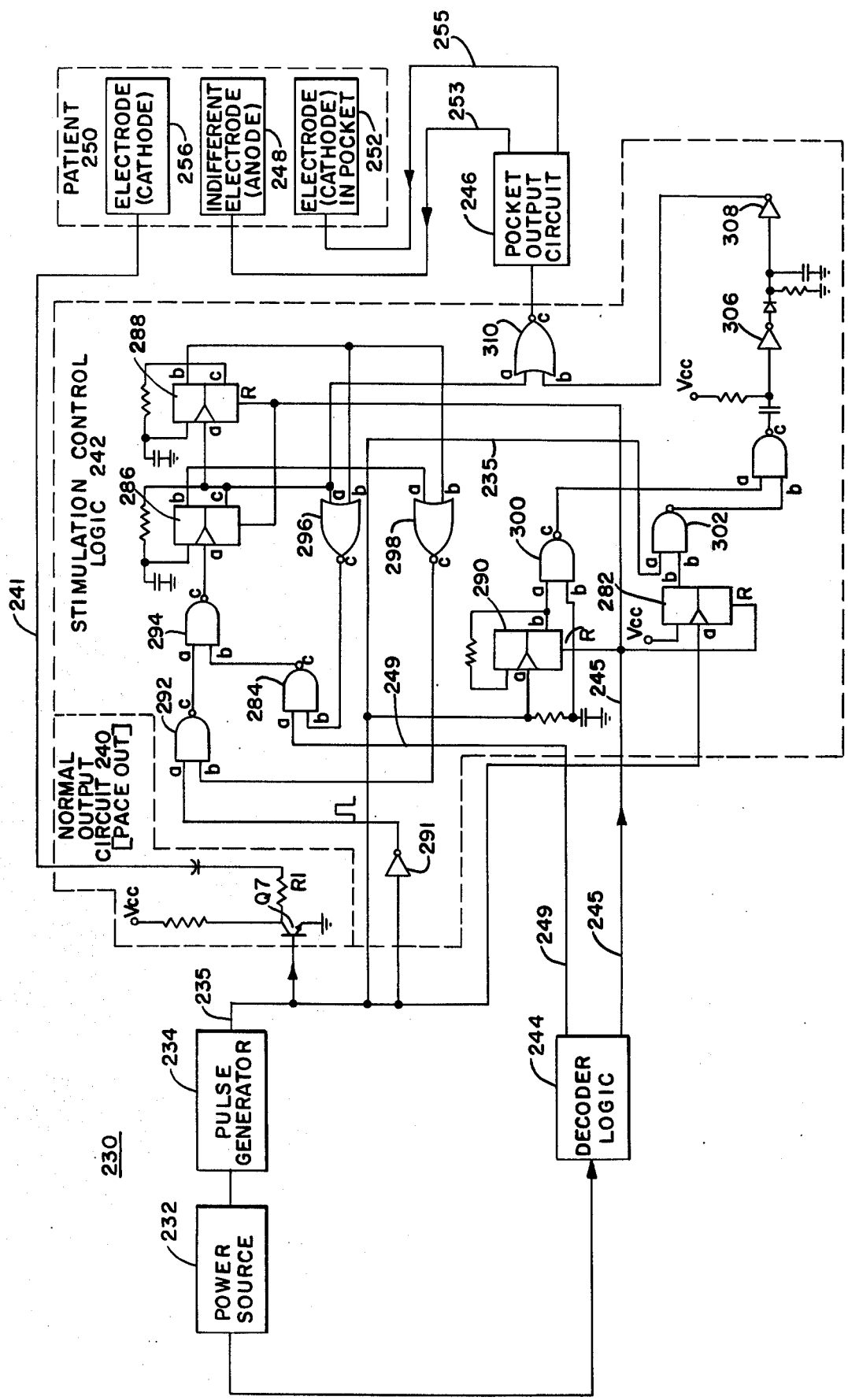
FIG. 4 is in part a block diagram and in part a schematic diagram of another embodiment of this invention including a logic circuit for detecting the initiation of the generation of pulses by a demand-type pacemaker, whereby a warning stimulation is given to the patient.

In a further, alternative embodiment of this invention as shown in FIG. 4, it is contemplated that a pacemaker 230 and in particular its pulse generator 234 may be of the demand type, such as disclosed in U.S. Pat. No. 3,478,746, assigned to the assignee of this invention, wherein the pacemaker monitors the patient's heart activity and is responsive thereto. Such a pacemaker does not generate and apply stimulating pulses to the heart if the patient's heart is operating normally. However, if the pacemaker senses that the patient's heart is beating at a rate below a predetermined level, the demand-type pacemaker 230 response to such a condition to initiate the generation of heart stimulating pulses, whereby the rate and also the level of energization to the heart is brought up to one that is acceptable. It is a common practice to implant such demand-type heart pacemakers prophylatically within patients whose hearts have not actually failed, but whose heart activity indicates that failure is imminent. Thus, if the patient's heart does fail in any respect, the demand-type pacemaker 230 will actuate a pulse generator 234 to initiate the application of energizing pulses to the patient's heart. The circuit of FIG. 4 closely resembles the circuit shown in FIGS. 2 and 3, and similar elements thereof are identified with similar numbers, but in the 200 and 300 series; their arrangement and operation have ben explained above. The present invention and in particular the stimulation logic control 242 as shown in FIG. 4, provides means for detecting the initiation of the generation of pulses by the pulse generator 234, whereby the stimulation control logic 242 is actuated by the pulses applied thereto via conductor 235 to apply energizing pulses via the pocket output circuit 246 to the electrodes 248 and 252 at a rate equal to that of the normal pacemaker output, thereby causing perceivable tissue stimulation of the pocket tissue. As described with respect to the pocket stimulation due to power source failure, such pocket stimulation in response to the initiation of the generation of stimulating pulses will continue until the patient or his physician resets the decoder logic 244 by applying a magnet once. In this manner, the patient is warned that a change of condition has occurred within his heart and that he should consult his physician to be checked for conditions leading to bradyarrhythmias resulting in the activation of the demand-type pacemaker. As indicated above, the stimulation control logic 242 functions to sense the initiation of the generation of the pulses from the pulse generator 234 of the demand-type pacemaker 230. In particular, the pulses are applied via conductor 235 through an inverter 291 to the "a" input terminal of NAND gate 292, to actuate the stimulation control logic 242 in a manner as explained in detail above, whereby warning stimulation is applied via pocket output circuit 246 to electrodes 248 and 252. At the same time, the pulses are applied via transistor Q7 of the normal output circuit 240, conductor 241 to the electrode 256 to apply the stimulating pulses to the patient's heart.

Numerous changes may be made in the above-described apparatus and the different embodiments of the invention may be made without departing from the spirit thereof; therefore, it is intended that all matter contained in the foregoing description and accompanying drawings shall be interpreted as illustrative and not in a limiting sense.

What is claimed is:

1. A self-contained body tissue stimulator to be implanted within the body of a patient, said stimulator comprising:
   (a) generator means including a power source, for providing a stimulating signal and having output terminals to be connected in-circuit with a first selected body tissue to be stimulated;
   (b) an auxiliary electrode to be connected in-circuit with a second selected body tissue to be stimulated;
   (c) detector means coupled to said output terminals for sensing the impedance presented therebetween and responsive to this impedance above a critical level for providing an output indicative thereof; and
   (d) logic means responsive to the detector means output for effecting the connection of said generator means to said auxiliary electrode, providing warning stimulation to the second selected body tissue, whereby the patient perceives the warning stimulation as an indication of the increased impedance presented to said generator means.

2. A body tissue stimulator as claimed in claim 1, wherein said detector means senses the impedance presented between said output terminals and is responsive to this impedance less than a second, critical level for providing an output indicative thereof.

3. A body tissue stimulator with a power source, as claimed in claim 1, wherein there is included a second detector means responsive to the voltage level of said power source to provide a second signal indicating that the voltage level of said power source has depleted below a predetermined level, said logic means responsive to the second signal for effecting the connection of said generator means to said auxiliary electrode, providing stimulation to said second selected body tissue, whereby the patient is made aware of the power source depletion.

4. A body tissue stimulator as claimed in claim 3, wherein said logic means responds to the first-mentioned signal to effect an application to said auxiliary electrode of a first warning signal of a first type, and to the second signal for providing a second warning signal of a second, different type.

5. A body tissue stimulator as claimed in claim 4, wherein said logic means provides the first warning signal as a first train of pulses at a first rate, and provides the second warning signal as a second train of warning pulses at a second, different rate, whereby the patient perceives a different stimulation and is able to identify the element that has failed or is about to fail.

6. A body tissue stimulator as claimed in claim 1, wherein said logic means comprises switch means responsive to manipulation exterior of the patient's body, for terminating the application of the warning stimulation to the second selected body tissue.

7. A body tissue stimulator as claimed in claim 6, wherein said logic means includes reset means responsive to a second type of actuation of said switch means, for resetting said logic means to be receptive to the signal of said detector means.

8. A body tissue stimulator as claimed in claim 1, wherein there is included a first output means for coupling the stimulating signal of said generator means in-circuit with the patient's heart, and a second switch means isolated from said first switch means for coupling the output of said logic means to said auxiliary electrode.

9. A heart pacemaker to be implanted within the body of a patient and energized by a power source, said pacemaker comprising:
   (a) generator means for providing a heart stimulating signal and having output terminals to be connected in-circuit with the patient's heart, whereby the stimulating signals are applied thereto;
   (b) an auxiliary electrode to be connected in-circuit with selected body tissue other than the patient's heart, whereby warning stimulation may be applied thereto;
   (c) first detector means coupled to said output terminals of said generator means for sensing the impedance presented therebetween and responsive to such an impedance above a critical level for providing a first warning signal indicative thereof;
   (d) second detector means coupled to the power source for sensing the voltage level thereof and for providing a second warning signal indicative that the source voltage is below a predetermined level; and
   (e) logic means responsive to the first warning signal for providing a first discrete type of warning stimulation to said auxiliary electrode, and to the second warning signal for providing a second, different discrete type of warning stimulation to said auxiliary electrode, whereby the element that has failed or is about to fail can be identified.

10. A heart pacemaker as claimed in claim 9, wherein there is included third detector means coupled to said output terminals of said generator means for sensing the impedance presented therebetween and responsive to such an impedance less than a second, critical level for providing a third warning signal indicative thereof.

11. A heart pacemaker as claimed in claim 9, wherein said logic means provides the first warning signal as a first train of pulses at a first rate, and provides the second warning signal as a second train of warning pulses at a second, different rate, whereby the patient perceives a different stimulation and is able to identify the element that has failed or is about to fail.

12. A heart pacemaker as claimed in claim 9, wherein said logic means contains switch means responsive to manipulation exterior of the patient's body, for terminating the application of the first and/or second warning stimulations to the second selected body tissue.

13. A heart pacemaker as claimed in claim 12, wherein said logic means includes reset means responsive to a second type of actuation of said switch means, for resetting said logic means to be receptive to the first and second warning signals of said first and second detector means.

14. A heart pacemaker as claimed in claim 9, wherein there is included a first output means for coupling the heart stimulating signal of said generator means in-circuit with the patient's heart, and a second switch means isolated from said first switch means for coupling the output of said logic means to said auxiliary electrode.

15. A body tissue stimulator to be implanted within the body of a patient and energized by a power source, said stimulator comprising:
(a) generator means for providing a first stimulus signal and having output terminals to be connected in-circuit with a first selected body tissue to be stimulated;
(b) an auxiliary electrode adapted to be connected in-circuit with a second selected body tissue to be stimulated;
(c) detector means coupled to said generator means for detecting an impending failure or failure of a parameter of said stimulator to stimulate body tissue and responsive thereto for providing a warning signal indicative thereof; and
(d) logic means responsive to the warning signal for effecting the connection of said generator means to said auxiliary electrode and for providing a second stimulus signal via said auxiliary electrode to second selected body tissue whereby the patient is made aware of the impending failure or failure of said stimulator to stimulate body tissue.

16. The combination of a body tissue stimulator to be implanted within the body of a patient and energized by a power source and control means external of the patient's body for applying actuating signals to said stimulator, said stimulator comprising:
(a) generator means for providing a first stimulus signal and having output terminals to be connected in-circuit with a first selected body tissue to be stimulated;
(b) an auxiliary electrode adapted to be connected in-circuit with a second selected tissue to be stimulated;
(c) first detector means coupled to said generator means for detecting an impedance as presented at the output of said generator means above a critical level and responsive thereto for providing a first warning signal indicative thereof;
(d) second detector means responsive to the voltage level of said power source for providing a second warning signal indicating that the voltage level of said power source has depleted below a predetermined level; and
(e) logic means responsive to each of the first and second warning signals for effecting connection of said generator means to said auxiliary electrode to provide a second stimulus signal to a second selected body tissue whereby the patient is made aware of the impending failure or failure, said logic means responsive to the actuating signal of said control means for resetting said logic means to respond again to the warning signal to detect the impending failure or failure to provide a further stimulus signal to the second selected body tissue and for terminating the application of the second stimulus signal to the second selected body tissue.

17. The combination as claimed in claims 16, wherein said logic means comprises switch means responsive to the actuating signal of said control means, for terminating the application of the second stimulus signal via said auxiliary electrode to the second selected body tissue.

18. The combination as claimed in claim 17, wherein said logic means includes reset means coupled to said switching means and responsive to the actuation of said switch means, for resetting said logic means to be receptive to the warning signal of said detector means.

19. The combination as claimed in claim 18, wherein said logic means responds to the first warning signal to effect an application to said warning means of a first stimulating signal of a first type, and to the second warning signal for providing a second stimulating signal of a second, different type.

20. The combination as claimed in claim 19, wherein said logic means provides the first stimulating signal as a first train of pulses at a first rate, and provides the second stimulating signal as a second train of warning pulses at a second, different rate, whereby the patient perceives a different stimulation and is able to identify the element that has failed or is about to fail.

21. A body tissue stimulator as claimed in claim 19, wherein there is included first output means for coupling the first stimulating signal of said generator means in-circuit with the patient's heart, and a second switch means isolated from said first switch means for coupling the output of said logic means to said warning means.

22. A body tissue stimulator to be implanted within the body of a patient, said stimulator comprising:
(a) generator means responsive to the rate of the patient's heart activity below a predetermined level for providing a heart stimulating signal and having output terminals adapted to be connected in-circuit with the patient's heart;
(b) an auxiliary electrode adapted to be connected in-circuit with a second selected body tissue to be stimulated;
(c) logic detector means coupled to said generator means and responsive to the initiation of the generation of the heart stimulating signal, for providing warning stimulation to the second selected body tissue, whereby the patient is made aware of the initiation of the generation of the heart stimulating signal by said generator means.

23. A body tissue stimulator to be implanted within the body of a patient and energized by a power source, said stimulator comprising:
(a) generator means for providing stimulus signals;
(b) detector means coupled to said generator means for detecting impending failure or failure of a component of said stimulator and responsive thereto for providing a warning signal indicative thereof;
(c) first output means for coupling the stimulus signals of said generator means in-circuit with a first selected tissue;
(d) second output means adapted for coupling the output of said generator means to a second selected tissue; and (e) logic means responsive to the warning signal for selectively providing the stimulus signals of said generator means to said second output circuit means, whereby the patient is made aware of the impending failure of said pacemaker component.

24. The body tissue stimulator as claimed in claim 23, wherein said first and second output means couple the first and second selected tissues in parallel with the output of said generator means.

25. The body tissue stimulator as claimed in claim 23, wherein each of said first and second output means includes a capacitor to be coupled between said generator output and the first and second selected body tissues to essentially block the passage of any DC signal to the first and second selected tissues.

* * * * *